United States Patent
Kersten et al.

(10) Patent No.: US 12,161,715 B2
(45) Date of Patent: *Dec. 10, 2024

(54) EGFR TARGETED THERAPY

(71) Applicants: Christian Kersten, Kristiansand (NO); Marte Grønlie Cameron, Kristiansand (NO); Svein Mjåland, Kristiansand (NO)

(72) Inventors: Christian Kersten, Kristiansand (NO); Marte Grønlie Cameron, Kristiansand (NO); Svein Mjåland, Kristiansand (NO)

(*) Notice: Subject to any disclaimer, the term of this patent is extended or adjusted under 35 U.S.C. 154(b) by 389 days.

This patent is subject to a terminal disclaimer.

(21) Appl. No.: 17/233,805

(22) Filed: Apr. 19, 2021

(65) Prior Publication Data
US 2021/0236635 A1 Aug. 5, 2021

Related U.S. Application Data

(63) Continuation of application No. 14/128,232, filed as application No. PCT/IB2012/001619 on Jul. 5, 2012, now Pat. No. 10,980,879.

(60) Provisional application No. 61/504,737, filed on Jul. 6, 2011.

(51) Int. Cl.
| | |
|---|---|
| C07K 16/28 | (2006.01) |
| A61K 31/517 | (2006.01) |
| A61K 31/5377 | (2006.01) |
| A61K 39/395 | (2006.01) |
| A61K 45/06 | (2006.01) |
| A61P 25/02 | (2006.01) |
| A61K 9/00 | (2006.01) |

(Continued)

(52) U.S. Cl.
CPC ........ *A61K 39/3955* (2013.01); *A61K 31/517* (2013.01); *A61K 31/5377* (2013.01); *A61K 39/39558* (2013.01); *A61K 45/06* (2013.01); *C07K 16/2863* (2013.01); *A61K 2039/505* (2013.01); *A61K 2039/507* (2013.01); *C07K 2317/21* (2013.01); *C07K 2317/24* (2013.01)

(58) Field of Classification Search
None
See application file for complete search history.

(56) References Cited

U.S. PATENT DOCUMENTS

| | | |
|---|---|---|
| 5,223,409 A | 6/1993 | Ladner |
| 5,565,332 A | 10/1996 | Hendricuhendricus |
| 5,585,089 A | 12/1996 | Queen |

(Continued)

FOREIGN PATENT DOCUMENTS

| | | |
|---|---|---|
| JP | 1-2007-532566 | 11/2007 |
| WO | WO 00/09675 | 2/2000 |

(Continued)

OTHER PUBLICATIONS

Kussie et al., A single engineered amino acid substitution changes antibody fine specificity.J Immunol. Jan. 1, 1994;152(1):146-52. (Year: 1994).*

(Continued)

*Primary Examiner* — Aurora M Fontainhas
(74) *Attorney, Agent, or Firm* — Casimir Jones, S.C.; J. Mitchell Jones

(57) ABSTRACT

The present invention relates to compositions and methods for treatment of neurological disorders. In particular, the present invention relates to EGFR as a clinical target for treatment of neurological disorders.

9 Claims, 2 Drawing Sheets

(51) Int. Cl.
 *A61K 39/00* (2006.01)
 *A61P 29/00* (2006.01)

(56) References Cited

U.S. PATENT DOCUMENTS

| | | | |
|---|---|---|---|
| 5,824,544 | A | 10/1998 | Armentano |
| 5,830,730 | A | 11/1998 | German |
| 5,872,154 | A | 2/1999 | Wilson |
| 5,885,808 | A | 3/1999 | Spooner |
| 5,906,820 | A | 5/1999 | Bacha |
| 5,981,225 | A | 11/1999 | Kochanek |
| 5,994,106 | A | 11/1999 | Kovesdi |
| 5,994,128 | A | 11/1999 | Fallaux |
| 5,994,132 | A | 11/1999 | Chamberlain |
| 6,001,557 | A | 12/1999 | Wilson |
| 6,019,978 | A | 2/2000 | Ertl |
| 6,033,908 | A | 3/2000 | Bout |
| 6,054,297 | A | 4/2000 | Carter |
| 6,180,370 | B1 | 1/2001 | Queen |
| 6,506,559 | B1 | 1/2003 | Fire |
| 7,893,036 | B2 | 2/2011 | Zamore |
| 8,481,064 | B2 | 7/2013 | McKay |
| 2008/0025958 | A1 | 1/2008 | Hannon |
| 2008/0269147 | A1 | 10/2008 | Tuschl |
| 2012/0094999 | A1 | 4/2012 | Gray et al. |

FOREIGN PATENT DOCUMENTS

| | | | |
|---|---|---|---|
| WO | WO 00/12738 | 3/2000 | |
| WO | WO 01/98537 | 12/2001 | |
| WO | WO 03/070966 | 8/2003 | |
| WO | WO 05/038054 | 4/2004 | |
| WO | WO 2005/023783 | 3/2005 | |
| WO | WO 05/054270 | 6/2005 | |
| WO | WO 2005/099756 | 10/2005 | |
| WO | WO-2005099756 A2 * | 10/2005 | ......... C07K 16/2863 |
| WO | WO 06/066048 | 6/2006 | |
| WO | WO 08/006369 | 1/2008 | |
| WO | WO 08/043753 | 4/2008 | |
| WO | WO 08/051306 | 5/2008 | |
| WO | WO2009/048947 | 4/2009 | |
| WO | WO-2009048947 A1 * | 4/2009 | ............ A61K 31/00 |
| WO | WO 2012/156437 | 11/2012 | |
| WO | WO 2013/005108 | 1/2013 | |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*
Alvarenga et al. "In-depth biophysical analysis of interactions between therapeutic antibodies and the extracellular domain of the epidermal growth factor receptor." Anal Biochem 2012;421:138-51.
Andres et al.: Quantitative automated microscopy (QuAM) elucidates growth factor specific signalling in pain sensitization, Molceular Pain 2010, 6:98.
Atalay et al., Novel therapeutic strategies targeting the epidermal growth factor receptor (EGFR) family and its downstream effectors in breast cancer. Ann Oncol 2003, 14:1346-1363.
Bohula et al., "RNA: Structure Metabolism and Catalysis: The Efficacy of Small Interfering RNAs Targeted to the Type 1 . . . " (J. Biol. Chem., 2003; 278: 15991-15997.
Bouhassira et al. "Prevalence of chronic pain with neuropathic characteristics in the general population." Pain 2008;136:380-7.
Breivik et al. "A new treatment principle for neuropathic pain? Approved oncologic drugs: Epidermal growth factor receptor (EGFR) inhibitors dramatically relieve severe neuropathic pain in a case series" Scandinavian Journal of Pain, vol. 4, No. 1, 2013, pp. 1-2.
Brown et al. "Gefitinib for the first-line treatment of locally advanced or metastatic non-small cell lung cancer." Health Technol Assess 2010;14:71-9.

Brummelkamp et al., "A System for Stable Expression of Short Interfering RNAs in Mammalian Cells," Science 2002; 296:550-3.
Calvo et al. "Following nerve injury neuregulin-1 drives microglial proliferation and neuropathic pain via the MEK/ERK pathway." Glia 2011;59:554-68.
Caplen et al., "Specific inhibition of gene expression by small double-stranded RNAs in invertebrate and vertebrate systems," Proc Natl Acad Sci U.S.A. 2001; 98: 9742-7.
Carell et al., "*A Novel Procedure for the Synthesis of Libraries Containing Small Organic Molecules*," Angew. Chem. Int. Ed. Engl. 33:2059-2061 [1994].
Carroll et al. "Expression of neuregulins and their putative receptors, ErbB2 and ErbB3, is induced during Wallerian degeneration." J Neurosci 1997;17:1642-59.
Chen-Plotikin et al., "Plasma EGF Levels predict cognitive decline in Parkinson's Disease" Ann Neurol. Apr. 2011;69(4):655-63.
Cho et al., "An Unnatural Biopolymer" Science 261:1303 [1993].
Ciardiello et al., Interaction between the epidermal growth factor receptor (EGFR) and the vascular endothelial growth factor (VEGF) pathways: a rational approach for multi-target anticancer therapy. Ann Oncol 2006, 17(Suppl 7):vii109-114.
Crips, C., et al., "Epidermal growth factor receptor targeted therapy in stages Ill and IV head and neck cancer," Jun. 2010, Current Oncology, Jun. 2010, vol. 17, No. 3, pp. 37-48.
Cull et al., "Screening for receptor ligands using large libraries of peptides linked to the C terminus of the lac repressor," Proc. Nad. Acad. Sci. USA 89:18651869 [1992].
Cwirla et al., "Peptides on phage: A vast library of peptides for identifying ligands," Proc. Natl. Acad. Sci. 87:6378-6382 [1990].
Devlin et al., "Random Peptide Libraries: A Source of Specific Protein Binding Molecules," Science 249:404-406 [1990].
DeWitt et al., "Diversomers: An approach to nonpeptide, nonoligomeric chemical diversity," Proc. Natl. Acad. Sci. U.S.A. 90:6909-6913 [1993].
Dieleman et al. "Incidence rates and treatment of neuropathic pain conditions in the general population." Pain 2008;137:681-8.
Dragnev et al., Bexarotene and erlotinib for aerodigestive tract cancer. J Clin Oncol 2005, 23:8757-8764.
Dworkin et al. "An overview of neuropathic pain: syndromes, symptoms, signs, and several mechanisms." Clin J Pain 2002;18:343-9.
Elbashir et al., "Functional anatomy of siRNAs for mediating efficient RNAi in *Drosophila melanogaster* embryo lysate," EMBO J. 2001; 20: 6877-88.
Elbashir et al., "RNA interference is mediated by 21-and 22-nucleotide RNAs" Genes Dev. 2001;15: 188-200.
Elbashir et al., "Duplexes of 21-nucleotide RNAs mediate RNA interference in cultured mammalian cells" Nature. 2001; 411:494-8.
Erschbamer et al., "Inhibitiing Epidermal Growth Factor Receptof Improves Structural, Locomotor, Sensory and Bladder Recovery from Experimental Spinal Cord Injury" The Journal of Neuroscience, Jun. 13, 2007 27(24):6428-6435.
Erb et al., "Recursive deconvolution of combinatorial chemical libraries" Proc. Nad. Acad. Sci. USA 91:11422-11426 [1994].
Felici, J. "Selection of Antibody Ligands from a Large Library of Oligopeptides Expressed on a Multivalent Exposition Vector" Mol. Biol. 222:301 [1991].
Finnerup et al. "The evidence for pharmacological treatment of neuropathic pain." Pain 2010;150:573-81.
Fodor "Multiplexed biochemical assays with biological chips" Nature 364:555-556 [1993].
Folprecht et al: Phase I pharmacokinetic/pharmacodynamic study of EKB-569, an irreversible inhibitor of the epidermal growth factor receptor tyrosine kinase, in combination with irinotecan, 5-fluorouracil, and leucovorin (FOLFIRI) in first-line treatment of patients with metastatic colorectal cancer. Clin Cancer Res 2008,14:215-223.
Gallop et al., "Applications of Combinatorial Technologies to Drug Discovery" J. Med. Chem. 37:1233 [1994].
Hofstetter et al. "Allodynia limits the usefulness of intraspinal neural stem cell grafts; directed differenation improves outcome." Nature Neuroscience, 2005, vol. 8, No. 3, pp. 346-353.

(56) References Cited

OTHER PUBLICATIONS

Holen et al., "Positional effects of short interfering RNAs targeting the human coagulation trigger Tissue Factor" Nucleic Acids Res. 2002; 30:1757-66.
Holt K. "Common side effects and interactions of colorectal cancer therapeutic agents." J Pract Nurs 2011;61:7-20.
Houghton "The Use of Synthetic Peptide Combinatorial Libraries for the Identification of Bioactive Peptides" Biotechniques 13:412-421 [1992].
International Search Report and Written Opinion mailed Dec. 12, 2012, PCT/IB2012/001619.
International Search Report and Written Opinion mailed Apr. 4, 2014, PCT/EP2013/003931.
Ise et al. "Overexpressed HER2 in NSCLC is a possible therapeutic target of EGFR inhibitors." Anticancer Res 2011;31:4155-62.
Overhoff et al., "Local RNA Target Structure Influences siRNA Efficacy: A Systematic Global Analysis" J Mol Biol. May 13, 2005;348(4):871-881.
Osawa et al., "Two Cases of Colorectal Cancer Patients with Poor Performance Status who had Unresectable Liver Metastasis Effectively treated by Cetuximab", Japan J. Cancer Chemotherapy, 2010, 37(11): 2189-2191.
Jensen et al. "The impact of neuropathic pain on health-related quality of life: review and implications" Neurology 2007;68:1178-82.
Jensen et al. "A new definition of neuropathic pain" Pain 2011;152:2204-5.
Ji RR. "Mitogen-activated protein kinases as potential targets for pain killers" Curr Opin Investig Drugs 2004;5:71-5.
Ji et al. "MAP kinase and pain" Brain Res Rev 2009;60(1):135-48.
Kanzaki et al. "Expression changes of the neuregulin 1 isoforms in neuropathic pain model rats." Neurosci Lett 2012;508:78-83.
Kersten et al., "Cetuximab alleviates neuropathic pain despite tumour progression," 2012, BMJ Case Reports 2012, vol. 2012.
Kersten et al. "Epithelial growth factor receptor (EGFR)-inhibition for relief of neuropathic pain—A case series", Scandinavian Journal of Pain, vol. 4, No. 1, 2013, pp. 3-7.
LAM "Application of combinatorial library methods in cancer research and drug discovery" Anticancer Drug Des., 1997, 12:145-167.
Lam "A new type of synthetic peptide library for identifying ligand-binding activity" Nature 354:82-84 [1991].
Maklad et al. "The EGFR is required for proper innervation to the skin" J. Invest. Dermatol. 2009;129(3):690-8.
Maughan et al. "Addition of cetuximab to oxaliplatin-based first-line combination chemotherapy for treatment of advanced colorectal cancer: results of the randomised phase 3 MRC COIN trial." Lancet 2011;377:2103-14.
Mesia Ricard et al., "Rapid palliation of symptoms with platinum-based chemotherapy plus cetuximab in recurrent oral cancer: a case report," Head & Neck Oncology, Biomed Central Ltd., London, UK, vol. 2, No. 1, Jan. 27, 2010, p. 3.
Nautiyal et al. "Emerging therapies in gastrointestinal cancers." World journal of gastroenterology : WJG 2006;12:7440-50.
Scuteri et al. "NGF protects dorsal root ganglion neurons from oxaliplatin by modulating JNK/Sapk and ERK1/2." Neurosci Lett. Dec. 17, 2010;486(3):141-5. Epub Sep. 17, 2010. PMID:20850503.
Kretschmer-Kazemi, et al., "The activity of siRNA in mammalian cells is related . . . " Nucleic Acids Res. Aug. 1, 2003;31(15):4417-24.
Oliveras-Ferraros et al. "Interferon/STAT1 and neuregulin signaling pathways are exploratory biomarkers of cetuximab (Erbitux(R)) efficacy in KRAS wild-type squamous carcinomas: a pathway-based analysis of whole human-genome microarray data from cetuximab-adapted tumor cell-line models." Int J Oncol 2011;39:1455-79.
Oyagi et al., "Forebrain specific heparin-binding epidermal growth . . . " Neuroscience. Jun. 30, 2011;185:116-24.

Petrelli et al. "Efficacy of EGFR Tyrosine Kinase Inhibitors in Patients With EGFR-Mutated Non-Small-Cell Lung Cancer: A Meta-Analysis of 13 Randomized Trials." Clin Lung Cancer 2012;13:107-14.
Ramanathan RK. "Alternative dosing schedules for cetuximab: a role for biweekly administration?" Clin Colorectal Cancer 2008;7:364-8.
Saadeh et al. "Panitumumab: a fully human monoclonal antibody with activity in metastatic colorectal cancer." Ann Pharmacother 2007;41:606-13.
Schamel et al. "Signal transduction: specificity of growth factors explained by parallel distributed processing" Med Hypotheses 1996;47:249-55.
Scholz et al. "The neuropathic pain triad: neurons, immune cells and glia" Nat Neurosci 2007;10:1361-8.
Liu et al. "Activation of epidermal growth factor receptors in astrocytes: from development to neural injury" J Neurosci Res 2007;85:3523-9.
Scott and Smith, "Searching for peptide ligands with an epitope library." Science 249:386-390 [1990].
Sohail et al., "Antisense oligonucleotides selected by hybridization . . . " Nucleic Acids Res., 2001; 29(10): 2041-2045.
Vincenzi et al. "The biological properties of cetuximab." Nov. 2008;68(2):93-106. Epub Aug. 3, 2008. Review.
Tuschl and Borkhardt, "Small interfering RNAs: a revolutionary tool for the analysis of gene function and gene therapy." Intervent. 2002; 2(3):158-67.
Tveit et al. "Randomized phase III study of 5-Fluouracil/Folinate/Oxaliplatin given continously or intermittently with or witout cetuximab: The Nordic VII Study (NCT00145314)." Ann Oncol 2010;21:viii1-viii12.
Vincenzi et al. "Cetuximab: from bench to bedside" Curr Cancer Drug Targets 2010;10:80-95.
Werner et al. "Localization of immunoreactive epidermal growth factor receptors in human nervous system" J. Histochem. Cytochem. 1988;36(1):81-6.
Wheeler et al. "Understanding resistance to EGFR inhibitors-impact on future treatment strategies." Nature reviews Clinical oncology 2010;7:493-507.
Xiang et al., "Short hairpin RNA-expressing bacteria elicit RNA interference in mammals." Nature 24: 6 (2006).
Xiong, H.Q., et al., "Cetuximab, A Monoclonal Antibody Targeting the Epidermal Growth Factor Receptor, in Combination with Gemcitabine for Advanced Pancreatic Cancer: A Multicenter Phase II Trial," Journal of Clinical Oncology, American Society of Clinical Oncology, US, vol. 22, No. 13, Jul. 1, 2004, pp. 2610-2616.
Yasuda et al."p38 MAP kinase inhibitors as potential therapeutic drugs for neural diseases" Cent Nerv Syst Agents Med Chem 2011;11:45-59.
Zuckennann et al., "Discovery of Nanomolar Ligands for o7-Transmembrane G-Protein-Coupled Receptors from a Diverse . . . " J. Med. Chem. 37: 2678-85 [1994].
Huang, Shyhmin et al. Dual-Agent Molecular Targeting of the Epidermal Growth Factor Receptor (EGFR): Combining Anti-EGFR Antibody with Tyrosine Kinase Inhibitor, Cancer Research, Aug. 2004, vol. 64, No. 15, p. 5355-5362.
Notice of Reasons for Refusal, Japanese Patent Application No. 2018-197322, mailed Dec. 9, 2019, 4 pages.
Boland, BA et al. Chemotherapy-induced neuropathy in cancer survivors. 2010, vol. 24, issue 2, from cancernetwork.com, retrieved Sep. 11, 2019, 3 web-based pages. (Year 2010).
Janjigian, YY et al. "Phase I/II trial of cetuximab and erlotinib in patients with lung adenocarcinoma and acquired resistance to erlotinib." Clin. Cancer Res. 2011, 17(8): 2521-2527.
Ramalingam, S. et al. Dual inhibition of the epidermal growth factor receptor with cetuximab, an IgG1 monoclonal antibody, and gefitinib, a tyroskine kinase inhibitor, in patients with refractory non-small cell lung cancer (NSCLC): a phase I study. J. Thoracic Oncology, 2008, 3(3): 258-264.
Simmons, CPL et al. "Clinical management of pain in advance lung cancer." Clinical Medicine Insights: Oncology, 2012, 6:331-346.
Erlotinib fact sheet, Chemocare.com, retrieved from internet Apr. 1, 2019.

(56) References Cited

OTHER PUBLICATIONS

Moyer M. Metals in medicine and the environment; Peripheral nueropathy and metals. Last modified Aug. 2009. Retrieved from faculty.virgina.edu/metals/cases/moyer2.html on May 27, 2018, 5 pages.

* cited by examiner

FIG. 1A
FIG. 1B
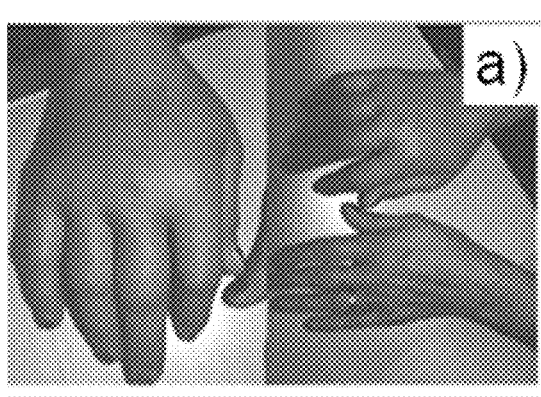
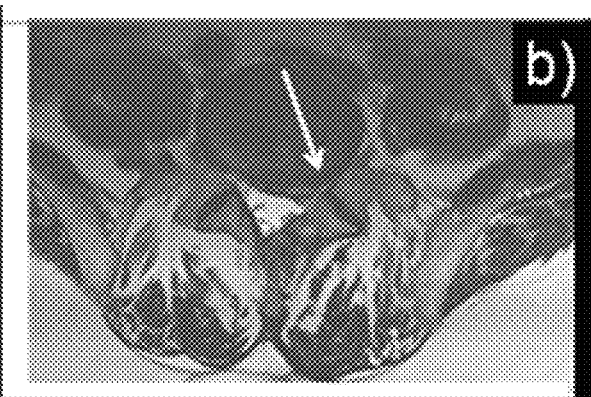
FIG. 1C
FIG. 1D
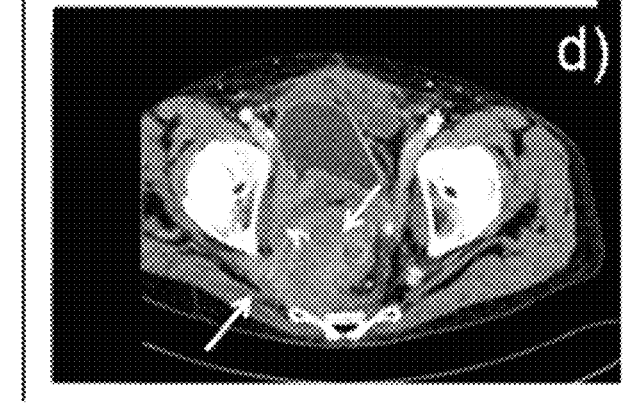

EGFR TARGETED THERAPY

CROSS-REFERENCE TO RELATED APPLICATIONS

The present application is a continuation of U.S. patent application Ser. No. 14/128,232, filed Jan. 6, 2014, now allowed as U.S. Pat. No. 10,980,879, which is a Section 371 U.S. national stage entry of International Patent Application No. PCT/IB2012/001619, International Filing Date Jul. 5, 2012, which published on Jan. 10, 2013 as Publication No. WO 2013/005108, which claims the benefit of U.S. Provisional Patent Application No. 61/504,737, filed Jul. 6, 2011, the contents of which are incorporated by reference in their entireties.

FIELD OF THE INVENTION

The present invention relates to compositions and methods for treatment of neurological disorders. In particular, the present invention relates to EGFR as a clinical target for treatment of neurological disorders.

BACKGROUND OF THE INVENTION

Chronic and/or neuropathic pain after nerve injury is a major health problem worldwide. Neuropathic pain (NP) is caused by a primary lesion or disease of the somatosensory system (Jensen T S, Baron R, Haanpaa M, et al. A new definition of neuropathic pain. Pain 2011; 152:2204-5). Not uncommonly, its severity, chronicity and the poor side-effect to benefit ratio of current pharmacotherapy for NP (Dworkin R H. An overview of neuropathic pain: syndromes, symptoms, signs, and several mechanisms. Clin J Pain 2002; 18:343-9; Finnerup N B, Sindrup S H, Jensen T S. The evidence for pharmacological treatment of neuropathic pain. Pain 2010; 150:573-81) lead to severely impaired physical and psychological functioning among sufferers (Jensen M P, Chodroff M J, Dworkin R H. The impact of neuropathic pain on health-related quality of life: review and implications. Neurology 2007; 68:1178-82). In the general population, the incidence of NP is estimated to be 1% (Dieleman J P, Kerklaan J, Huygen F J, Bouma P A, Sturkenboom M C. Incidence rates and treatment of neuropathic pain conditions in the general population. Pain 2008; 137:681-8) and rising (Dworkin, supra). The resulting prevalence of moderate to severe chronic NP is 5% (Bouhassira D, Lanteri-Minet M, Attal N, Laurent B, Touboul C. Prevalence of chronic pain with neuropathic characteristics in the general population. Pain 2008; 136:380-7), making it a common and formidable health problem worldwide.

Despite the numerous etiologies of NP, the mechanism of its perpetuation, regardless of origin, appears to involve the interaction of neuronal, glial and immune cells (Scholz J, Woolf C J. The neuropathic pain triad: neurons, immune cells and glia. Nat Neurosci 2007; 10:1361-8). Communication between these cells has been attributed to signaling via the family of mitogen-activated protein kinase (MAPK) proteins (Ji R R, Gereau R Wt, Malcangio M, Strichartz G R. MAP kinase and pain. Brain Res Rev 2009; 60:135-48).

Neuropathic pain is a complex, chronic pain state that usually is accompanied by tissue injury. With neuropathic pain, the nerve fibers themselves may be damaged, dysfunctional or injured. These damaged nerve fibers send incorrect signals to other pain centers. The impact of nerve fiber injury includes a change in nerve function both at the site of injury and areas around the injury. Some neuropathic pain studies suggest the use of non-steroidal anti-inflammatory drugs, such as Aleve or Motrin, may ease pain. Some people may require a stronger painkiller, such as those containing morphine. Anticonvulsant and antidepressant drugs seem to work in some cases. If another condition, such as diabetes, is involved, better management of that disorder may alleviate the pain.

In cases that are difficult to treat, a pain specialist may use invasive or implantable device therapies to manage the pain. Electrical stimulation of the nerves involved in neuropathic pain generation may also control the pain symptoms.

Unfortunately, neuropathic pain often responds poorly to standard pain treatments and occasionally may get worse instead of better over time. For some people, it can lead to serious disability. Current treatments are characterized by an unsatisfactory side effect to benefit-ratio.

Thus, additional therapies that target neurological disorders such as neuropathic pain are urgently needed.

SUMMARY OF THE INVENTION

The present invention relates to compositions and methods for treatment of neurological disorders. In particular, the present invention relates to EGFR (Epidermal Growth Factor Receptor) as a clinical target for treatment of neurological disorders.

Accordingly, in some embodiments, the present invention provides methods of treating a subject with a neurological disorder comprising administering to said subject an agent that inhibits at least one biological function of an EGFR polypeptide. In some embodiments, the subject exhibits symptoms of a neurological disorder and said administering said agent reduces or modulates symptoms of said neurological disorder. In some embodiments, the reagent is an antigen binding protein that specifically binds to said EGFR polypeptide. In some embodiments, the antigen binding protein is selected from the group consisting of bevacizumab, cetuximab, conatumumab, ganitumab, matuzumab, necitumumab, nimotuzumab, panitumumab, rilotumumab, trastuzumab, and zalutumumab. In some embodiments, the antigen binding protein is preferably selected from the group consisting of Cetuximab or Panitumumab. In some embodiments, the reagent is a small molecule drug. In some embodiments, the small molecule drug is selected from the group consisting of afatinib, erlotinib, gefitinib, lapatinib, neratinib and vandetanib. In some embodiments, the small molecule drug is preferably selected from the group consisting of Gefitinib and Erlotinib. In some embodiments, the subject is in an animal. In some embodiments, the animal is a human. In some embodiments, the subject does not have cancer or has not been previously treated for cancer. In some embodiments, the neurological disorder is neuropathic pain. In some embodiments, the neurological disorder is selected from the group consisting of pain, sciatica, multiple sclerosis, depression, dementia, Parkinson's disease, stroke, axotomy, and ischemia or reperfusion injury, Down's syndrome and autism. In some embodiments, the agent that inhibits at least one biological function of an EGFR polypeptide is co-administered with at least additional therapeutic agent. In some embodiments, the at least additional therapeutic agent is selected from the group consisting of non-steroidal anti-inflammatory drugs, steroidal anti-inflammatory drugs, opioid-based drugs, antidepressants, anticonvulsants, antiepileptics, anti-anxiety drugs, and cannibinoids and combinations thereof.

In some embodiments, the present invention provides methods of treating a neurological disorder, comprising administering a reagent that inhibits at least one biological function of an EGFR polypeptide to a subject exhibiting symptoms of a neurological disorder, wherein said administering reduces, modulates or eliminates said symptoms. In some embodiments, the agent that inhibits at least one biological function of an EGFR polypeptide is co-administered with at least additional therapeutic agent. In some embodiments, the at least additional therapeutic agent is selected from the group consisting of non-steroidal anti-inflammatory drugs, steroidal anti-inflammatory drugs, opioid-based drugs, antidepressants, anticonvulsants, antiepileptics, anti-anxiety drugs, and cannibinoids and combinations thereof.

In some embodiments, the present invention provides for use of an agent that inhibits at least one biological function of an EGFR for the treatment of a neurological disorder. In some embodiments, the neurological disorder is selected from the group consisting of neuropathic pain, sciatica, multiple sclerosis, depression, dementia, Parkinson's disease, stroke, ischemia or reperfusion injury, axotomy, Down's syndrome and autism. In some embodiments, the reagent is an antigen binding protein that specifically binds to said EGFR polypeptide. In some embodiments, the antigen binding protein is selected from the group consisting of bevacizumab, cetuximab, conatumumab, ganitumab, matuzumab, necitumumab, nimotuzumab, panitumumab, rilotumumab, trastuzumab, and zalutumumab. In some embodiments, the antigen binding protein is preferably selected from the group consisting of Cetuximab or Panitumumab. In some embodiments, the reagent is a small molecule drug. In some embodiments, the small molecule drug is selected from the group consisting of afatinib, erlotinib, gefitinib, lapatinib, neratinib and vandetanib. In some embodiments, the small molecule drug is preferably selected from the group consisting of Gefitinib and Erlotinib. In some embodiments, the agent that inhibits at least one biological function of an EGFR polypeptide is co-administered with at least additional therapeutic agent. In some embodiments, the at least additional therapeutic agent is selected from the group consisting of non-steroidal anti-inflammatory drugs, steroidal anti-inflammatory drugs, opioid-based drugs, antidepressants, anticonvulsants, antiepileptics, anti-anxiety drugs, and cannibinoids and combinations thereof. In some embodiments, the administration or coadministration reduces or modulates symptoms of said neurological disorder.

Additional embodiments are described herein.

DESCRIPTION OF THE FIGURES

FIG. 1A-D provides graphic depictions of treatments according to the present invention. a) Case 2. Photographs depicting the persistence of abnormalities typical of CRPS1, in the patient's right hand. Treatment with the EGRF inhibitor cetuximab relieved her NP but did not influence the vasomotor pathology of the underlying condition. b) Case 3. Magnetic resonance image taken six weeks postoperatively, due to recurrence of NP back pain, after initial relief. The image demonstrates pathological scar tissue formation around the patient's fifth lumbar spinal nerve root. c and d) Case 4. Computed tomography scan of the patient's pelvis before c) and after d) EGFR-inhibition. In the interval between the scans, the patient was completely relieved of his NP despite a growing pelvic tumor which increasingly invaded sacral nerves.

DEFINITIONS

Figure 2:
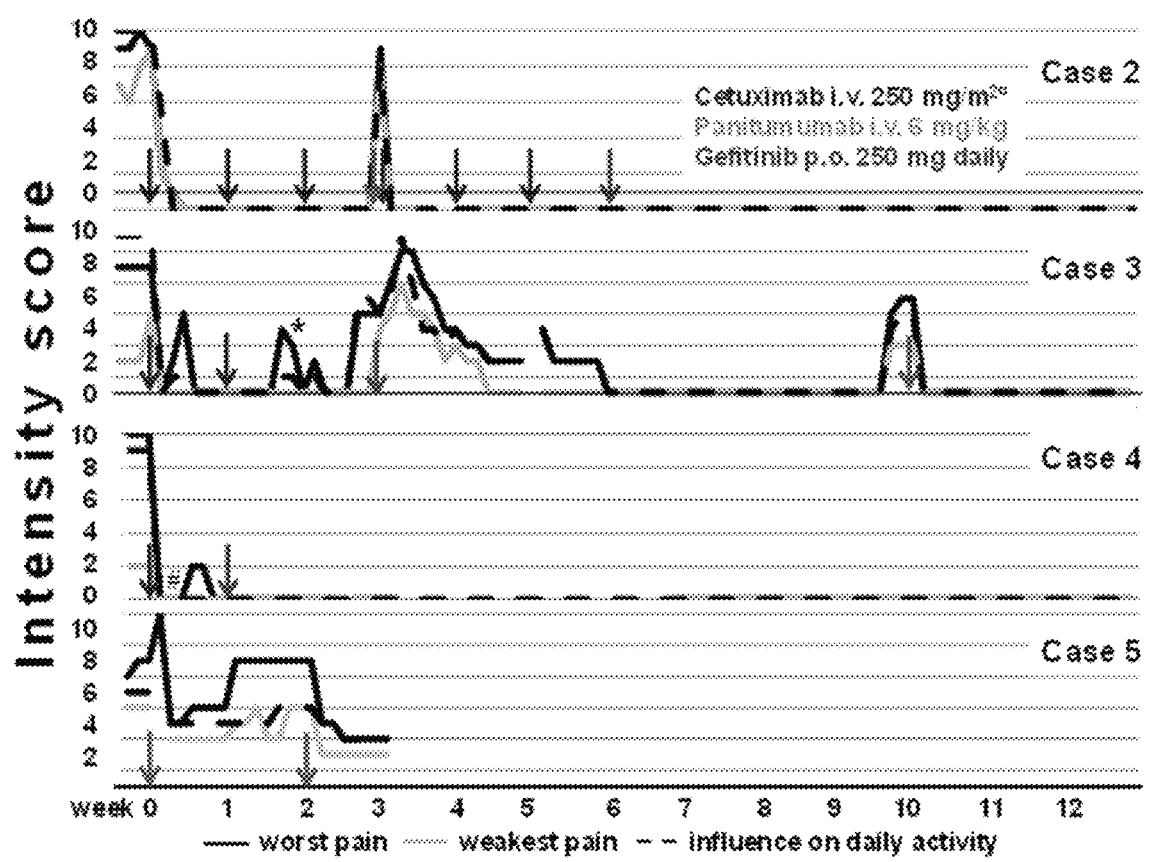
FIG. 2 provides graphs of BPI-measurements before and after introduction of EGFR-inhibition.

To facilitate an understanding of the present invention, a number of terms and phrases are defined below:

As used herein, the term "neuropathic pain" refers to a complex, chronic pain state that usually is accompanied by tissue injury. Neuropathic pain includes, but is not limited to, the following syndromes and disease states: nerve impingement, complex regional pain syndrome types I and II, trigeminal neuralgia, phantom pain, diabetic neuropathy, spinal cord injury, and nerve damage due to i.e. cancer, burns and trauma.

As used herein, the term "inhibits at least one biological activity of EGFR" refers to any agent that decreases any activity of EGFR (e.g., including, but not limited to, the activities described herein), via directly contacting EGFR protein, contacting EGFR mRNA or genomic DNA, causing conformational changes of EGFR polypeptides, decreasing EGFR protein levels, or interfering with EGFR interactions with signaling partners like different potential ligands including, but not limited to EGF, TGF-alpha, Neuregulin, NGF and/or homo- and heterodimers of receptors including, but not limited to HER1, HER2, HER3 and HER4, and affecting the expression of EGFR target genes. Inhibitors also include molecules that indirectly regulate EGFR biological activity by intercepting upstream signaling molecules.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., neurological disorders). Test compounds comprise both known and potential therapeutic compounds. A test compound can be determined to be therapeutic by screening using the screening methods described herein. In some embodiments, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the described compositions and methods.

DETAILED DESCRIPTION OF THE INVENTION

The present invention relates to compositions and methods for treatment of neurological disorders. In particular, the present invention relates to EGFR as a clinical target for treatment of neurological disorders.

I. Therapeutic Applications

The present invention relates to compositions and methods for treatment of neurological disorders. In particular, the present invention relates to EGFR as a clinical target for treatment of neurological disorders.

EGF-MAPK-signalling is activated in neurons and glial cells in response to injury or dysfunction. Inhibition of the EGFR may interrupt a negative feedback loop, thereby alleviating symptoms from neurological disorders, like (pain, neuropathic pain, MS, depression, dementia, Parkinson's disease, stroke, axotomy, etc.). Especially in neuropathic pain, the pathological sensitization of nerve fibers for pain is inhibited.

Pain due to nerve injury is thought to be generated and sustained by MAPK signalling via the three pathways ERK, p38 and JNK in central, spinal and peripheral nerves, as well as in peripheral and central glia such as astrocytes and Schwann cells (Ji R R, Gereau R Wt, Malcangio M, Strichartz G R. MAP kinase and pain. Brain Res Rev 2009; 60(1):135-48). Furthermore, communication between neuronal cells, glial cells and immune cells is an established pathogenic factor in neuropathic pain (Scholz J, Woolf C J. The neuropathic pain triad: neurons, immune cells and glia. Nat. Neurosci. 2007; 10(11):1361-8). Activation of and communication between these cells after nerve injury has been shown to be dependent on MAPK signalling, potentially activated by EGFR, which is upregulated in the nervous system (Werner M H, Nanney L B, Stoscheck C M, King L E. Localization of immunoreactive epidermal growth factor receptors in human nervous system. J. Histochem. Cytochem. 1988; 36(1):81-6; Maklad A, Nicolai J R, Bichsel K J, Evenson J E, Lee T C, Threadgill D W, et al. The EGFR is required for proper innervation to the skin. J. Invest. Dermatol. 2009; 129(3):690-8; Ji R R. Mitogen-activated protein kinases as potential targets for pain killers. Curr Opin Investig Drugs 2004; 5(1):71-5).

The activation of the MAPK-signalling pathways is of established importance in neurological diseases and neuropathic pain. EGFR-inhibition blocks several of these pathways effectively (JNK, RAS-MEK-ERK, STAT, etc). Embodiments of the present invention provide methods of treating neurological disorders by inhibiting EGFR. The present invention is not limited to a particular neurological disorder. For example, in some embodiments, the present invention provides methods of inhibiting the EGF receptor to treat pain, neuropathic pain, MS, depression, dementia, Parkinson's disease, stroke, ischemia and reperfusion injury, ischemic brain injury, and axotomy. See e.g., Oyagi et al., Neuroscience. 2011 Jun. 30; 185:116-24 and Chen-Plotikin et al., Ann Neurol. 2011 April; 69(4):655-63. It is also contemplated that administration of the agents of the present invention is useful for ameliorating symptoms associated with genetics disorders such as Downs syndrome and autism.

Experiments conducted during the course of development of embodiments of the present invention demonstrated a dramatic, immediate and repetitive pain reduction without tumor regression in a patient with neuropathic pain. This effect was observed in a patient treated with Cetuximab.

Accordingly, the present invention provides methods of utilizing a reagent that inhibits at least one biological function of an EGFR polypeptide to reduce, ameliorate or modulate, or provide prophylaxis, for one or more symptoms associated with the following diseases or disorders: pain, neuropathic pain, sciatica, MS, depression, dementia, Parkinson's disease, stroke, ischemia and reperfusion injury, ischemic brain injury, axotomy, Down's syndrome and autism.

A. Antibody Therapy

In some embodiments, the present invention utilizes antibodies that target EGFR. Any suitable antibody (e.g., monoclonal, polyclonal, or synthetic) may be utilized in the therapeutic methods disclosed herein.

In some embodiments, neurological disorders such as neuropathic pain are treated with an antigen binding protein. Suitable antigen binding proteins include, but are not limited to, bevacizumab, cetuximab, conatumumab, ganitumab, matuzumab, necitumumab, nimotuzumab, panitumumab, rilotumumab, Trastuzumab, and zalutumumab. In some preferred embodiments, the monoclonal antibody Cetuximab (Eli Lilly and Company, New York, N.Y.) is used. Cetuximab is a recombinant chimeric human murine immunoglobulin G1 antibody that binds to the extra-cellular domain of epidermal growth factor receptor with a higher affinity than either endogenous ligand. This binding inhibits receptor phosphorylation and activation and it leads to receptor internalization and degradation. (The biological properties of cetuximab. Vincenzi B, Schiavon G, Silletta M, Santini D, Tonini G. Crit Rev Oncol Hematol. 2008 November; 68(2): 93-106. Epub 2008 Aug. 3. Review). Cetuximab is licensed to treat cancer, and is most often used in colorectal cancer without K-RAS mutation in the EGF-signalling pathway. Cetuximab was developed to inhibit EGFR-activation, leading to the further inhibition of several pathways, among others, MAPK-signalling. This IgG1 antibody is used in colorectal cancer to inhibit the activation by the ligand EGF, but since it blocks the EGFR it inhibits binding of other EGF-binding ligands as well. In other preferred embodiments, the monoclonal antibody panitumumab is utilized (Amgen, Thousand Oaks, Calif.).

In preferred embodiments, the antigen binding proteins are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In preferred embodiments, antibody based therapeutics are formulated as pharmaceutical compositions as described below. In preferred embodiments, administration of an antibody composition of the present invention results in a measurable decrease in symptoms of a neurological disorder.

B. RNA Interference and Antisense Therapies

In some embodiments, the present invention utilizes agents that modulate the expression of EGFR. For example, in some embodiments, the present invention employs compositions comprising oligomeric antisense or RNAi compounds, particularly oligonucleotides (e.g., those described herein), for use in modulating the function of nucleic acid molecules encoding EGFR, ultimately modulating the amount of EGFR expressed.

1. RNA Interference (RNAi)

In some embodiments, RNAi is utilized to inhibit EGFR protein function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference).

An important factor in the design of siRNAs is the presence of accessible sites for siRNA binding. Bahoia et al., (J. Biol. Chem., 2003; 278: 15991-15997; herein incorporated by reference) describe the use of a type of DNA array called a scanning array to find accessible sites in mRNAs for designing effective siRNAs. These arrays comprise oligonucleotides ranging in size from monomers to a certain maximum, usually CoCmers, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7 mers to 25 mers), where it is important to achieve a compromise between oligonucleotide length and binding affinity, to retain efficacy and target specificity (Sohail et al, Nucleic Acids Res., 2001; 29(10): 2041-2045). Additional methods and concerns for selecting siRNAs are described for example, in WO 05054270, WO05038054A1, WO03070966A2, J Mol Biol. 2005 May 13; 348(4):883-93, J Mol Biol. 2005 May 13; 348(4):871-81, and Nucleic Acids Res. 2003 Aug. 1; 31(15):4417-24, each of which is herein incorporated by reference in its entirety. In addition, software (e.g., the MWG online siMAX siRNA design tool) is commercially or publicly available for use in the selection of siRNAs.

In some embodiments, the present invention utilizes siRNA including blunt ends (See e.g., US20080200420, herein incorporated by reference in its entirety), overhangs (See e.g., US20080269147A1, herein incorporated by reference in its entirety), locked nucleic acids (See e.g., WO2008/006369, WO2008/043753, and WO2008/051306, each of which is herein incorporated by reference in its entirety). In some embodiments, siRNAs are delivered via gene expression or using bacteria (See e.g., Xiang et al., Nature 24: 6 (2006) and WO06066048, each of which is herein incorporated by reference in its entirety).

In other embodiments, shRNA techniques (See e.g., 20080025958, herein incorporated by reference in its entirety) are utilized. A small hairpin RNA or short hairpin RNA (shRNA) is a sequence of RNA that makes a tight hairpin turn that can be used to silence gene expression via RNA interference. shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA polymerase III.

2. Antisense

In other embodiments, EGFR expression is modulated using antisense compounds that specifically hybridize with one or more nucleic acids encoding EGFR and/or EGFR. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of EGFR. In the context of the present invention, "modulation" means either an increase (stimulation) or a decrease (inhibition) in the expression of a gene. For example, expression may be inhibited to treat a neurological disorder.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a EGFR. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon"

refer to the codon or codons that are used in vivo to initiate translation of an mRNA molecule transcribed from a gene encoding EGFR.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in PCT Publ. No. WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

C. Genetic Therapy

The present invention contemplates the use of any genetic manipulation for use in modulating the expression of EGFR. Examples of genetic manipulation include, but are not limited to, gene knockout (e.g., removing the EGFR gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct). Genetic therapy may also be used to deliver siRNA or other interfering molecules that are expressed in vivo (e.g., upon stimulation by an inducible promoter).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subjects in a variety of ways. For example, in some embodiments of the present invention, vectors are administered into cells using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

D. Small Molecule Therapy

Some embodiments of the present invention utilize small molecules that inhibit one or more biological activities of EGFR. Small molecule therapeutics are identified, for example, using the drug screening methods described herein. In some embodiments, the small molecule therapeutics useful in the present invention include, but are not limited to, afatinib, erlotinib, gefitinib, lapatinib, neratinib and vandetanib. In some preferred embodiments, the small molecule is gefitinib or erlotinib, tradenamed Iressa (AstraZeneca, London, UK) and Tarceva (Genentech, South San Fransisco, Calif.), respectively) (Activation of epidermal growth factor receptors in astrocytes: from development to neural injury. Liu B, Neufeld A H. J Neurosci Res. 2007 December; 85(16):3523-9. Review).

E. Pharmaceutical Compositions

The present invention further provides pharmaceutical compositions (e.g., comprising pharmaceutical agents that modulate the expression or activity of EGFR) for use in the methods described above. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention also include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active pharmaceutical agent with the pharmaceutical carrier(s) or excipient(s). In general the formulations are prepared by uniformly and intimately bringing into association the active ingredients with liquid carriers or finely divided solid carriers or both, and then, if necessary, shaping the product.

The pharmaceutical compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual agents, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the agent is administered in maintenance doses, ranging from 0.01 µg to 100 g per kg of body weight, once or more daily, to once every 20 years.

F. Combination Therapy

In some embodiments, the present invention provides therapeutic methods comprising one or more compositions described herein (e.g., EGFR inhibitors) in combination with an additional agent (e.g., an agent for treating neurological disorders or neuropathic pain). The present invention is not limited to a particular agent. Examples include, but are not limited to: anti-inflammatory agents such as NSAIDs and steroids; opioid pain killers; antidepressants such as tricyclics and serotonin-noepinephrine reuptake inhibitors (SNRIs); anticonvulsants such as gabapentin; antiepileptics; benzodiazapines; anti-anxiety drugs such as selective serotonin reuptake inhibitors (SSRIs); dietary supplements such as alpha lipoic acid and benfotiamine; cannabinoids; and the like.

Classes of useful agents for combination therapy include, for example, non-steroidal anti-inflammatory drugs (NSAIDS) such as Aspirin (Anacin, Ascriptin, Bayer, Bufferin, Ecotrin, Excedrin), Choline and magnesium salicylates (CMT, Tricosal, Trilisate), Choline salicylate (Arthropan), Celecoxib (Celebrex), Diclofenac potassium (Cataflam), Diclofenac sodium (Voltaren, Voltaren XR), Diclofenac sodium with misoprostol (Arthrotec), Diflunisal (Dolobid), Etodolac (Lodine, Lodine XL), Fenoprofen calcium (Nalfon), Flurbiprofen (Ansaid), Ibuprofen (Advil, Motrin, Motrin IB, Nuprin), Indomethacin (Indocin, Indocin SR), Ketoprofen (Actron, Orudis, Orudis KT, Oruvail), Magnesium salicylate (Arthritab, Bayer Select, Doan's Pills, Magan, Mobidin, Mobogesic), Meclofenamate sodium (Meclomen), Mefenamic acid (Ponstel), Meloxicam (Mobic), Nabumetone (Relafen), Naproxen (Naprosyn, Naprelan), Naproxen sodium (Aleve, Anaprox), Oxaprozin (Daypro), Piroxicam (Feldene), Rofecoxib (Vioxx), Salsalate (Amigesic, Anaflex 750, Disalcid, Marthritic, Mono-Gesic, Salflex, Salsitab), Sodium salicylate (various generics), Sulindac (Clinoril), Tolmetin sodium (Tolectin), Valdecoxib (Bextra); steroidal anti-inflammatory drugs including hydrocortisone, prednisone, methylprednisolone, beclomethasone, beclomethasone, budesonide, flunisolide, fluticasone propionate, triamcinolone and the like; and opiate-based pain killers including, but not limited to, fentanyl, hydromorphone, methadone, morphine, oxycodone, and oxymorphone; antidepressants, including tricyclic compounds such as bupropion, nortriptyline, desipramine, amitriptyline, amitriptylinoxide, butriptyline, clomipramine, demexiptiline, dibenzepin, dimetacrine, dosulepin/dothiepin, doxepin, imipramine, amineptine, iprindole, opipramol, tianeptine, trimipramine, imipraminoxide, lofepramine, melitracin, metapramine, nitroxazepine, noxiptiline, pipofezine, propizepine, protriptyine, and quinupramine and SNRIs such as duloxetine, venlafaxine, desvenlafaxine, milnacipran, levomilnacipran, sibutramine, bicifadine, and SEP-227162; anticonvulsants such as pregabalin, gabapentin, carbamazepine, and oxcarbazepine and benzodiazepines (e.g., alprazolam, bretazenil, bromazepam, brotizolam, chlordiazepoxide, cinolazepam, clonazepam, clorazepate, clotiazepam, cloxazolam, delorazepam, diazepam, estazolam, etizolam, flunitrazepam, flurazepam, flutoprazepam, halazepam, ketazolam, loprazolam, lorazepam, lormetazepam, medazepam, midazolam, nemetazepam, nitrazepam, nordazepam, oxazepam, phenazepam, pinazepaam, prazepam, premazepam, quazepam, temazepam, tetrazepam, triazolam, clobazam, DMCM, flumazenil, eszopiclone, zaleplon, zolpidem, and zopiclone); selective serotonin re-uptake inhibitors (SSRIs) such as citalopram, dapoxetine, escitalopram, fluoxetine, fluvoxamine, indalpin, paroxetine, sertraline, and zimelidine; and cannabinoids such as delta-9-tetrahydrocannabinol and nabilone.

III. Drug Screening Applications

In some embodiments, the present invention provides drug screening assays (e.g., to screen for drugs that inhibit EGFR). The screening methods of the present invention utilize EGFR. For example, in some embodiments, the present invention provides methods of screening for compounds that alter (e.g., decrease) the expression of EGFR. The compounds or agents may interfere with transcription, by interacting, for example, with the promoter region. The compounds or agents may interfere with mRNA produced from EGFR (e.g., by RNA interference, antisense technologies, etc.). The compounds or agents may interfere with pathways that are upstream or downstream of the biological activity of EGFR. In some embodiments, candidate compounds are antisense or interfering RNA agents (e.g., oligonucleotides) directed against EGFR. In other embodiments, candidate compounds are antibodies or small molecules that specifically bind to EGFR and inhibit its biological function.

In one screening method, candidate compounds are evaluated for their ability to alter EGFR expression by contacting a compound with a cell expressing EGFR and then assaying for the effect of the candidate compounds on expression. In some embodiments, the effect of candidate compounds on expression of EGFR is assayed for by detecting the level of EGFR mRNA expressed by the cell. mRNA expression can be detected by any suitable method.

In other embodiments, the effect of candidate compounds on expression of EGFR is assayed by measuring the level of polypeptide encoded by EGFR. The level of polypeptide expressed can be measured using any suitable method.

Specifically, the present invention provides screening methods for identifying modulators, i.e., candidate or test compounds or agents (e.g., antibodies, proteins, peptides, peptidomimetics, peptoids, small molecules or other drugs) which bind to EGFR, have an inhibitory effect on, for example, EGFR expression or activity, or have a stimulatory or inhibitory effect on, for example, the expression or activity of a EGFR substrate. Compounds thus identified can be used to modulate the activity of target gene products (e.g., EGFR) either directly or indirectly in a therapeutic protocol, to elaborate the biological function of the target gene product, or to identify compounds that disrupt normal target gene interactions. Compounds that inhibit the activity or expression of EGFR are useful in the treatment of neurological disorder.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364:555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249:404-406 [1990]; Cwirla et al., Proc. Natl. Acad. Sci. 87:6378-6382 [1990]; Felici, J. Mol. Biol. 222: 301 [1991]).

EXPERIMENTAL

The following examples are provided in order to demonstrate and further illustrate certain preferred embodiments and aspects of the present invention and are not to be construed as limiting the scope thereof.

Example 1

A 68 year old male with metastatic colon cancer suffered from neuropathic pain due to a pelvic recurrence impinging on his sciatic nerve. Over the course of several years he was treated with potent opioid analgesics, antiepileptics, antidepressants, antiinflammatories, radiotherapy, chemotherapy, hyperbaric oxygen and acupuncture, in an attempt to relieve this pain. These treatments were only marginally effective and dose-escalation was limited by side-effects.

After approximately three years, the patient was given the combination of XELOX chemotherapy (capecitabine and oxaliplatin) and the EGFR antibody, Cetuximab, in yet another effort to shrink his pelvic tumor and thereby relieve his pain. At the outset of this treatment the patient required 200 mg dolcontin per 24 hours. At his first follow-up appointment, after two treatments, he reported that he had practically stopped all opiate use. A pelvic MRI, taken four months later, showed no change in the pelvic tumor size although the neuropathic pelvic pain was completely gone at that point.

During subsequent treatment breaks, the patient's pain recurred and he required higher doses of opiates. However, at each subsequent reintroduction of XELOX and Cetuximab, analgesic response was repeated and the pain completely, or nearly completely, disappeared within four to five hours.

After 22 months of treatment with XELOX and Cetuximab, the patient's lung metastases progressed and both chemotherapy and antibody treatment were discontinued. Over the subsequent months, the patient's pain increased dramatically and his depot opiate dose escalated to 320 mg/24 hours, without satisfactory effect. After approximately four months of worsening pain, without any tumor-directed treatment, Cetuximab monotherapy 450 mg i.v./250 mg per m2 was reinstated in an attempt to relieve his pain. Once again, within hours after the first infusion of Cetuximab, the patient's pain improved dramatically and he was able to cut his depot opiate dose in half within the subsequent four weeks.

For the next 20 months, while his cancer was clearly in progression, the patient continued to receive Cetuximab infusions roughly every 12 days for pain relief. Despite the development of symptoms and complications from his metastatic disease, the chronic pelvic neuropathic pain continued to be best controlled with Cetuximab.

In order to test whether the analgesic effect of this rather expensive medication was dose-dependent, the patient was given 20% of the normal Cetuximab dose (the patient was unaware of this change) which resulted in no analgesic effect. The Cetuximab dose was therefore increased to the previously effective dose and he continued to receive infusions approximately every 12 days, with effective analgesia reached within 4-5 hours, lasting just under 2 weeks. During the last few days before a new infusion, the patient required higher doses of opiates, but this could be reduced again to approximately ⅓rd of the dose immediately following subsequent Cetuximab infusion.

Eight months after starting Cetuximab monotherapy for analgesia, MRI of the pelvis showed an increase in the offending lesion. Despite this finding, Cetuximab continued to have the dramatic analgesic response described and the patient was able to maintain a much better quality of life.

Example 2

We recently reported our experience in treating NP in a rectal cancer patient with cetuximab, (Kersten C, Cameron M G. Cetuximab alleviates neuropathic pain despite tumour progression. BMJ Case Rep 2012; 2012) a monoclonal antibody against the epidermal growth factor (EGF) receptor, which consequently inhibits MAPK-signaling (Vincenzi B, Zoccoli A, Pantano F, Venditti O, Galluzzo S. Cetuximab: from bench to bedside. Curr Cancer Drug Targets 2010; 10:80-95). The patient repeatedly experienced dramatic relief of NP just hours after cetuximab infusion despite progressive pelvic tumor invasion of sacral plexus nerves, suggesting a direct anti-NP effect.

Since EGFR-inhibitors have been widely tested in clinical trials and are approved oncologic drugs with primarily transient and manageable side effects, we have offered this treatment to five patients with chronic, debilitating and therapy-resistant NP (Holt K. Common side effects and interactions of colorectal cancer therapeutic agents. J Pract Nurs 2011; 61:7-20; Petrelli F, Borgonovo K, Cabiddu M, Barni S. Efficacy of EGFR Tyrosine Kinase Inhibitors in Patients With EGFR-Mutated Non-Small-Cell Lung Cancer: A Meta-Analysis of 13 Randomized Trials. Clin Lung Cancer 2012; 13:107-14; Brown T, Boland A, Bagust A, et al. Gefitinib for the first-line treatment of locally advanced or metastatic non-small cell lung cancer. Health Technol Assess 2010; 14:71-9).

Case Series:

Since December, 2011, we have treated three non-cancer patients, one bladder cancer patient and one pancreatic cancer patient with intravenous (cetuximab, panitumumab) and oral (gefitinib) EGFR-inhibitors for excruciating and longstanding NP, see Table 1. Two of three non-cancer patients (cases 2 and 3) and both cancer patients (cases 4 and 5) responded within 24 hours, with a mean decrease in worst pain from 9 to 1 as documented on the Brief Pain Inventory, short form (BPI) (21, 22) see FIG. 2. Three patients (cases 2, 4 and 5) who were taking analgesics for their NP at the time of first EGFR-inhibition, have been able to reduce the doses significantly. Follow-up to date is 7-148 days for those who have responded to treatment.

TABLE 1

Baseline characteristics of the patients.

| Case | Age, Sex | Neuropathic pain history | Pain detect score# | Severe functional impairment according to BPI | | Specialist referrals or pain mangement | Previous treatments for neuropathic pain |
|---|---|---|---|---|---|---|---|
| 1 | 53, male | Six-year History of progressive peripheral polyneuropathy of unclear aetiology (possibly Borrelia-related). | 30/38 | Genaral activity: Mood: Walking ability: Normal work: Relationships: Sleep: Enjoyment of life: | 9 9 10 10 8 9 8 | Neurologist Rheumatologist Anaesthesiologist Tertiary care pain unit | Paracetamol NSIADs Steroids Antiepileptics Antidepressents* Healing KIOVIG (ivig) Physical exercise-distraction therapy)* |
| 2 | 53, female | Eight-month history of complex regional pain syndrome type 1 (CRPS1) of the right hand. | 31/38 | General activity: Mood Walking ability: Normal work: Relationships: Sleep: Enjoyment of life: | 10 5 0 10 5 10 7 | Orthopedic surgeon Neurologist Rheumatologist Anesthesiologist Tertiary care pain unit | Paracetamol* NSIADs* Steroids* Weak opiates* Antiepileptics* Antidepressants Nerve Blocks Clonidine Physical therapy Cognitive behavioral therapy |
| 3 | 63, male | Eight-month history of radiculopathy due to failed back surgery syndrome (FBSS) with scar tissue formation at the L4/L5 level. | 26/38 | General activity: Mood: Walking ability: Normal work: Relationships: Sleep: Enjoyment of life: | 10 8 9 9 8 8 8 | Neurosurgeon Primary care physician | Antiepileptics Opiates |
| 4 | 57, male | Twenty-month history of a bladder cancer recurrence invading pelvic organs, muscles and sacral nerve roots. | 24/38 | General activity: Mood: Walking ability: Normal work: Relationships: Sleep: Enjoyment of life: | 9 7 7 9 7 3 10 | Oncologist Palliative care specialist Anesthesiologist | Paracetamol* Steroids* Opiates* Antiepileptics* Antidepressants* Chemotherapy* Palliative pelvic radiation |

*treatments still in use at the time of the patients' first infusion of cetuximab
according to the Pain Detect tool, a score between 19 and 38 makes a neuropathic component of pain more than 90% probable. (16)

Response to Treatment:

The patients were asked to complete a BPI short form daily, just before and during the EGFR inhibition, in order to document their neuropathic pain and thus, help us to judge their responses and guide treatment decisions. The patients' scores are summarized in FIG. 2.

Case 1 was given three weekly infusions of cetuximab. The treatment had no effect on the patient's NP and after the 3rd dose, treatment was discontinued (data not shown).

Case 2 was given a total of six weekly infusions of cetuximab (FIG. 2, red arrows). Within 24 hours after the first cetuximab dose, the patient experienced complete pain relief which persisted until the next infusion. After three weekly infusions of cetuximab, with continuous response, treatment with the monoclonal antibody panitumumab was attempted (FIG. 2, blue arrow). Due to its pharmacokinetic properties, this extracellular EGFR-inhibitor is administered biweekly. It was therefore given in an attempt to simplify the treatment procedure for the patient. However, the patient reported recurrence of severe pain on the very same evening as the panitumumab infusion. She received a therapeutically successful infusion of cetuximab on the following day. After a total of six infusions of cetuximab, EGFR-inhibition was converted to the oral small molecule inhibitor, gefitinib, so that the patient could be free to travel abroad on a holiday.

Gefitinib was started seven days after the last cetuximab infusion and the patient did not experience pain recurrence after conversion to tablets. At the present time, which is 15 weeks after her first gefitinib dose, and 21 weeks after her first cetuximab infusion, the patient's NP continues to be completely resolved. EGFR inhibition has had no effect on the vasomotor symptoms that accompany CRPS1. However, the pain relief has enabled the patient to comply with intensive physiotherapy, which was previously hampered by extreme levels of pain. As a consequence, there appears to be an indirect improvement in the edema that otherwise complicates her condition and that can lead to permanent disability.

Case 3 was given two weekly infusions of cetuximab (FIG. 2, red arrows). Again, within hours after the first infusion, the patient's severe and persistent pain was reduced significantly and in the following days, the NP disappeared completely. After his second dose of cetuximab, the patient waited to start a new treatment until pain recurrence. After an eleven-day cetuximab wash-out, his NP began to relapse.

At that stage, the patient converted to gefitinib tablets (FIG. 2, green arrow). His pain continued to increase for the first two days of oral treatment. However, from the third dose of gefitinib, the pain gradually improved to levels as good as those he had experienced with cetuximab. The patient's NP was so well-controlled by both cetuximab and gefitinib that he could resume his physically active outdoorsman-lifestyle. However, the patient developed pneumonia one month after starting gefitinib. Dyspnoea persisted after treatment of the pneumonia and interstitial lung disease (ILD) could not be excluded. Gefitinib was therefore discontinued (see FIG. 2) and NP recurred after three days. A dose of panitumumab was subsequently given and NP diminished on the very same evening and he was again free from pain. When, after approximately three weeks, his pain recurred, pregabalin, a drug approved for the treatment of NP, was attempted. He had previously been unsuccessfully treated with gabapentin, also approved for the treatment of NP, but due to the uncertainty surrounding the possibility of ILD, an attempt at conventional treatment was felt to be warranted before further treatment with an oral EGFR inhibitor. The patient responded to pregabalin, and continues to be pain-free at 19 weeks follow-up.

Case 4 was given cetuximab after treatment with the combination of gabapentin, amitriptyline, paracetamol, steroids, and titration to a 24-hour morphine-equivalent dose of 1800 mg failed to control his NP. Within hours after the infusion of the EGFR inhibitor, the patient experienced complete relief of his NP for the first time in over six months. Just three days after the first cetuximab treatment, his opiate and gabapentin doses were reduced by 50%, limited by the fear of abstinence symptoms and rebound effects that can be associated with abrupt discontinuation of these substances. Cetuximab was converted to oral gefitinib at the time of the next planned treatment (FIG. 2, green arrow). Complete relief from NP was maintained through and beyond this transition, and despite progressive tumor invasion of pelvic nerves (see FIG. 1). His neuropathic pain continues to be completely relieved by gefitinib at the present time (follow-up of 18 weeks).

Case 5 received panitumumab while she was being treated with palliative gemcitabine for metastatic pancreatic cancer. Despite having symptomatic cancer, chronic phantom-limb pain radiating down her left leg was her major complaint. She had developed stump atrophy, contractures and pain which prohibited the use of her prosthesis. Consequently, she was confined to a wheelchair. Within hours after the infusion of panitumumab, her phantom limb pain decreased to 50% (see FIG. 2). She subsequently required less breakthrough pain medication, was able to sleep through the night and her health-related quality of life (QOL) improved. The intensity of worst pain recurred to baseline levels after more intensive physiotherapy, but was again effectively alleviated within one day after the second infusion of panitumumab (follow-up 3 weeks to date).

Discussion

We suggest the effective alleviation of NP to be a potential class effect of EGFR-inhibitors, since all three tested drugs were effective. The successful analgesic treatment of NP in two non-cancer patients and two cancer patients with different underlying mechanisms of pain is consistent with the effect described in our previous report. Four of the five patients offered this treatment experienced dramatic and rapid analgesic responses after long-standing NP refractory to standard treatments.

Both extracellular (cetuximab and panitumumab) and intracellular (gefitinib) EGFR-inhibition led to complete NP relief.

Further support for a genuine drug effect is derived from the correlation between EGFR inhibitor pharmacokinetics and the clinical observations in case 3. The fact that the patient's pain recurred 11 days after his last cetuximab infusion and roughly 20 days after panitumumab is consistent with the half life of these drugs (Ramanathan R K. Alternative dosing schedules for cetuximab: a role for biweekly administration? Clin Colorectal Cancer 2008; 7:364-8; Saadeh C E, Lee H S. Panitumumab: a fully human monoclonal antibody with activity in metastatic colorectal cancer. Ann Pharmacother 2007; 41:606-13) and with observations from our previously reported case (Kersten C, Cameron M G. Cetuximab alleviates neuropathic pain despite tumour progression. BMJ Case Rep 2012; 2012). In addition, the fact that the patient's pain responded more slowly to the oral drug than to intravenous administration of both cetuximab and panitumumab, supports the hypothesized causal and direct effect of EGFR inhibition.

Case 2 reported a dramatic increase in pain just hours after infusion of the anti-EGFR antibody panitumumab. A recent study has demonstrated that cetuximab and panitumumab hinder each other's EGFR binding (Alvarenga M L, Kikhney J, Hannewald J, et al. In-depth biophysical analysis of interactions between therapeutic antibodies and the extracellular domain of the epidermal growth factor receptor. Anal Biochem 2012; 421:138-51). This may possibly have led to the displacement of cetuximab by panitumumab and thereby caused the rapid pain recurrence observed in case 2. All anti-EGFR drugs employed in these patients were developed to inhibit EGFR1-activation and, amongst others, MAPK-signalling by EGF in cancers. The observed effect may be due to inhibition of EGF, but by blocking EGFR1, these drugs also have the potential to inhibit other EGFR1-binding ligands (Wheeler D L, Dunn E F, Harari P M. Understanding resistance to EGFR inhibitors-impact on future treatment strategies. Nature reviews Clinical oncology 2010; 7:493-507), either directly or by inhibition of human epidermal growth factor receptor (HER) family heterodimerization (Nautiyal J, Rishi A K, Majumdar A P. Emerging therapies in gastrointestinal cancers. World journal of gastroenterology: WJG 2006; 12:7440-50; Schamel W W, Dick T P. Signal transduction: specificity of growth factors explained by parallel distributed processing. Med Hypotheses 1996; 47:249-55; Ise N, Omi K, Nambara D, Higashiyama S, Goishi K. Overexpressed HER2 in NSCLC is a possible therapeutic target of EGFR inhibitors. Anticancer Res 2011; 31:4155-61). It is in that respect of interest, that the neuregulin 1-ErbB3-ErbB2 complex has recently been suggested to be a causal mechanism in nerve injury-induced trigeminal neuropathic pain in rats (Ma F, Zhang L, Westlund K N. Trigeminal Nerve Injury ErbB3/ErbB2 Promotes Mechanical Hypersensitivity. Anesthesiology 2012).

Several receptor tyrosine kinases (RTKs) have the potential to activate MAPK-signaling, which has been proposed as a target for therapies directed against NP, as well as other chronic neurological diseases (Ji 2009, supra; Ji R R. Mitogen-activated protein kinases as potential targets for pain killers. Curr Opin Investig Drugs 2004; 5:71-5; Yasuda S, Sugiura H, Tanaka H, Takigami S, Yamagata K. p38 MAP kinase inhibitors as potential therapeutic drugs for neural diseases. Cent Nery Syst Agents Med Chem 2011; 11:45-59). After nerve injury, neurons upregulate members of the HER-family of receptors (Scholz, supra; Liu B, Neufeld A H. Activation of epidermal growth factor receptors in astrocytes: from development to neural injury. J Neurosci Res 2007; 85:3523-9; Carroll S L, Miller M L, Frohnert P W, Kim S S, Corbett J A. Expression of neuregulins and their putative receptors, ErbB2 and ErbB3, is induced during Wallerian degeneration. J Neurosci 1997; 17:1642-59), thereby potentially increasing their activation of the MAPK signaling (Ji, 2009, supra) cascade. This may lead to further interaction between cells in the neuropathic pain triad (Scholz, supra). We have therefore previously hypothesized a direct inhibition of MAPK-signaling by cetuximab in neuronal or glial cells (Kersten C, Cameron M G. Cetuximab alleviates neuropathic pain despite tumor progression. BMJ Case Rep 2012).

Neuregulin is an important regulator of the neuropathic pain triad (Calvo M, Zhu N, Grist J, Ma Z, Loeb J A, Bennett D L. Following nerve injury neuregulin-1 drives microglial proliferation and neuropathic pain via the MEK/ERK pathway. Glia 2011; 59:554-68). Expression changes in neuregulin 1 isoforms in NP model rats suggest a link between the EGFR and NP (Kanzaki H, Mizobuchi S, Obata N, et al. Expression changes of the neuregulin 1 isoforms in neuropathic pain model rats. Neurosci Lett 2012; 508:78-83). Furthermore, neuregulin signaling pathways have been shown to be biomarkers of cetuximab efficacy (Oliveras-Ferraros C, Vazquez-Martin A, Queralt B, et al. Interferon/STAT1 and neuregulin signaling pathways are exploratory biomarkers of cetuximab (Erbitux®) efficacy in KRAS wild-type squamous carcinomas: a pathway-based analysis of whole human-genome microarray data from cetuximab-adapted tumor cell-line models. Int J Oncol 2011; 39:1455-79).

After many months of excruciating NP, leading to severely impaired physical and psychosocial functioning, all four responding patients almost immediately regained a QOL that was previously unimaginable.

Example 3

A 72-year-old patient with metastatic colon cancer (metastatic only to her lungs) was started on third-line treatment with panitumumab monotherapy. She came to her first follow-up appointment 14 days after the first infusion and spontaneously reported that she had experienced complete relief in her intermittent sciatica which she had had for over six months, within 24 hours of her first infusion of panitumumab. She has subsequently received two additional doses (at 2-week intervals) and remains pain-free, at five weeks of follow-up. She retrospectively describes her sciatica as intermittent, graded 6 to 8 on a 10-point scale and until treatment with the EGFR-inhibitor was begun, it was present on most days, at times greatly limiting her activities and mobility. Since treatment was started, the pain has not recurred and she reports that her quality of life has improved significantly. Previous treatments for this condition included paracetamol, NSAIDs and benzodiazepines. She no longer requires analgesics and there were no concurrent interventions or other changes in her medications.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method of treating a human subject to relieve neuropathic pain comprising:
administering an agent that inhibits EGFR (Epidermal Growth Factor Receptor) to a subject exhibiting symptoms of a neuropathic pain condition selected from the group consisting of phantom limb pain, complex regional pain syndrome I, complex regional pain syndrome II, trigeminal neuralgia, diabetic neuropathy, neuropathic pain due to nerve impingement, and failed back surgery syndrome, wherein said subject is not receiving opioid therapy and said administering reduces, modulates or eliminates said neuropathic pain condition, and further wherein the agent that inhibits EGFR is selected from the group consisting of a small molecule drug agent selected from the group consisting of afatinib, erlotinib, gefitinib, lapatinib, and neratinib and a monoclonal antibody selected from the group consisting of cetuximab, panitumumab, necitumumab, and nimotuzumab.

2. The method of claim 1, wherein the treated subject exhibits symptoms of neuropathic pain and said treatment reduces or modulates symptoms of neuropathic pain.

3. The method of claim 1, wherein said agent that inhibits EGFR is selected from the group consisting of cetuximab and panitumumab.

4. The method of claim 1, wherein said agent that inhibits EGFR is selected from the group consisting of erlotinib and gefitinib.

5. The method of claim 1, wherein said neuropathic pain condition is phantom limb pain.

6. The method of claim 1, wherein said neuropathic pain condition is complex regional pain syndrome I.

7. The method of claim 1, wherein said neuropathic pain condition is complex regional pain syndrome IL.

8. The method of claim 1, wherein said neuropathic pain condition is trigeminal neuralgia.

9. The method of claim 1, wherein said neuropathic pain condition is diabetic neuropathy.

* * * * *

UNITED STATES PATENT AND TRADEMARK OFFICE
CERTIFICATE OF CORRECTION

| | | |
|---|---|---|
| PATENT NO. | : 12,161,715 B2 | Page 1 of 1 |
| APPLICATION NO. | : 17/233805 | |
| DATED | : December 10, 2024 | |
| INVENTOR(S) | : Christian Kersten et al. | |

It is certified that error appears in the above-identified patent and that said Letters Patent is hereby corrected as shown below:

In the Claims

Column 24, Claim 7, Line 44 reads:
condition is complex regional pain syndrome IL
Whereas it should read:
condition is complex regional pain syndrome II Signed and Sealed this
Twenty-eighth Day of January, 2025

Coke Morgan Stewart
*Acting Director of the United States Patent and Trademark Office*